United States Patent [19]

Savas

[11] Patent Number: 5,273,536
[45] Date of Patent: Dec. 28, 1993

[54] TAPERED BALLOON CATHETER

[76] Inventor: Vicky Savas, 18300 S. Dr., Apt. 85, Southfield, Mich. 48076

[21] Appl. No.: 862,466

[22] Filed: Apr. 2, 1992

[51] Int. Cl.$^5$ ............................................. A61M 29/00
[52] U.S. Cl. ..................................... 604/96; 606/194
[58] Field of Search ............................. 604/96–103, 604/280, 282, 52, 53; 606/191–194

[56] References Cited

U.S. PATENT DOCUMENTS

| | | |
|---|---|---|
| 4,195,637 | 4/1980 | Grüntzig et al. |
| 4,323,071 | 4/1982 | Simpson et al. |
| 4,456,000 | 6/1984 | Schjeldahyl et al. |
| 4,689,041 | 8/1987 | Corday et al. ............... 604/96 X |
| 4,832,691 | 5/1989 | Witzel ........................... 604/96 |
| 4,896,670 | 1/1990 | Crittenden. |
| 5,059,178 | 10/1991 | Ya ............................... 604/96 |

OTHER PUBLICATIONS

Banka, et al., Effectiveness Of Decremental Diameter Balloon Catheters (Tapered Balloon), *The American Journal of Cardiology*, vol. 69, p. 188 (Jan. 15, 1992).

*Primary Examiner*—John D. Yasko
*Attorney, Agent, or Firm*—Gifford, Groh, Sprinkle, Patmore and Anderson

[57] ABSTRACT

An improved balloon for use in percutaneous transluminal coronary angioplasty. The improved balloon has a working section with a length greater than about 30 mm and a frusto-conical shape when inflated. The frusto-conical working section being tapered from the proximal end to the distal end to conform to the shape of the vessel to be dilated. The balloon may be used in connection with any dilatation catheter.

3 Claims, 1 Drawing Sheet

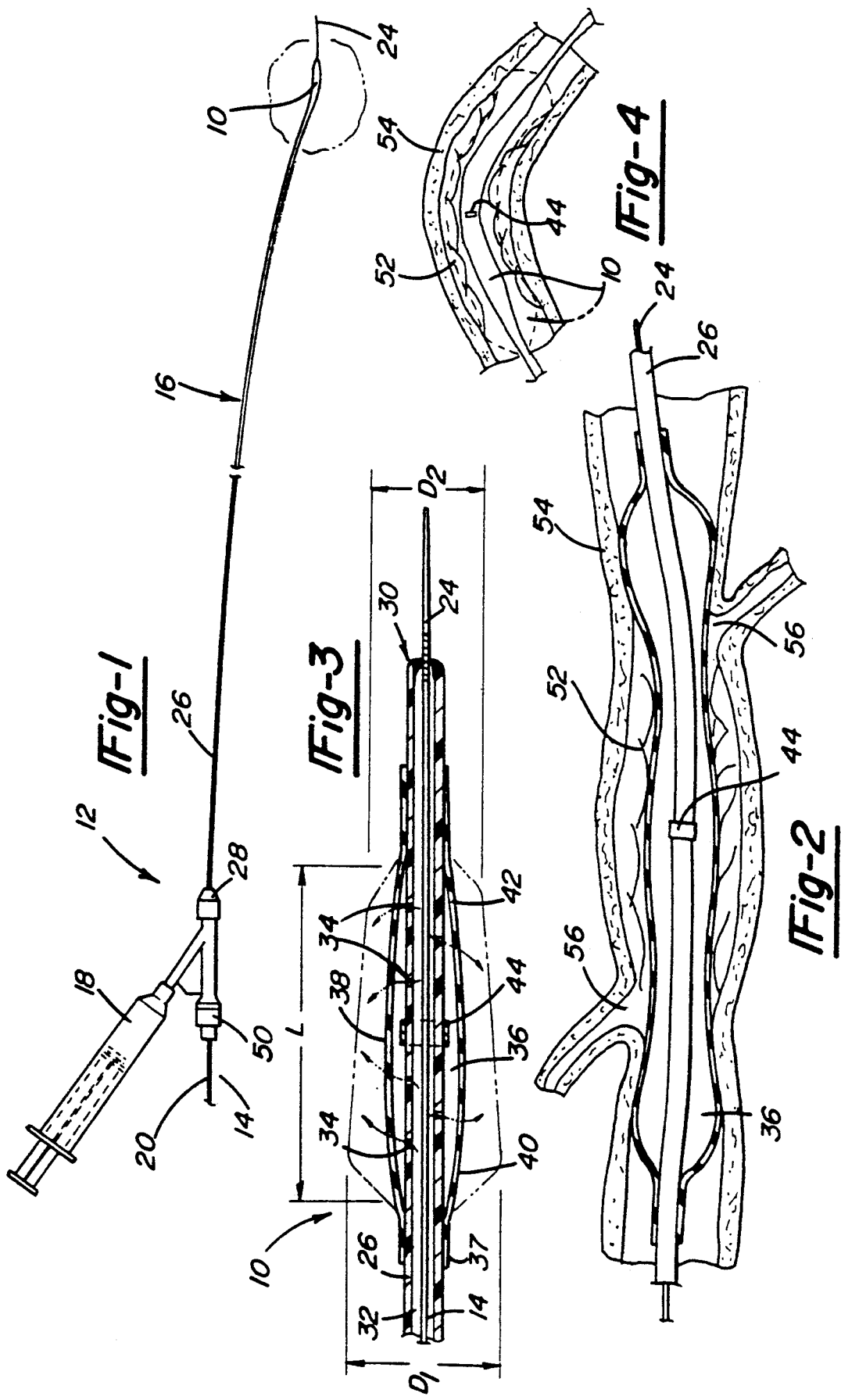

TAPERED BALLOON CATHETER

BACKGROUND OF THE INVENTION

I. Field of the Invention

The present invention is directed to a balloon dilatation catheter for use in the treatment of occluded arteries such as in heart disease, and more particularly, to a long balloon structure for use in tapered or bent blood vessels.

II. Prior Art

Percutaneous transluminal coronary angioplasty (PTCA) is a well known method for myocardial revascularization. The method consists of using a balloon catheter such as disclosed in U.S. Pat. No. 4,323,071 to Simpson et al to open or dilate stenoses or lesions located in blood vessels. Simpson et al disclose a catheter system having an inflatable short balloon mounted on a dilatation element support hose. The catheter system is percutaneously introduced into the body via the femoral artery. The catheter system is advanced through the vascular system over a guide wire and the balloon is positioned within the stenosis to be opened. Inflation liquid is then introduced into the interior of the balloon through the catheter system by a hand syringe to inflate the balloon. Inflation of the balloon causes a dilatation of the plaque forming the lesion. The plaque is compressed against the wall of the vessel resulting in increased blood vessel lumen size with increased blood flow.

Although PTCA has been very successful in treatment of stenoses, it has been found that the length of the lesion is an important factor in the success of PTCA. As reported by Ryan et al in "Guidelines For Percutaneous Transluminal Coronary Angioplasty: A Report Of The ACC/AHA Task Force on Assessment of Diagnostic and Therapeutic Cardiovascular Procedures" in *J Am Coll Cardiol* 1988; 12:527–545, lesions exceeding 2 cm in length have a low procedural success rate and a high rate of subsequent major cardiac events such as abrupt closure, death, myocardial infarction, or dissection during the procedure. In the event of severe dissection or closure, bypass surgery is usually required. Ryan et al also recorded that the success rate of PTCA is reduced significantly when lesions are located at sharp bends in the vessel. For instance, lesions located in a vessel having a bend angle of 45° but less than 90° have been associated with moderate success (60–85%) and complication rates. However, when the lesions are located in a bend having an angle of greater than 90°, the success rate decreases to less than 60% and the complication rate increases. Lesions which are both long and located on a bend represent a significantly greater risk of complication than lesions having only one of those characteristics. See Ellis et al *American Journal of Cardiology*, 1990, 66:932-7.

Conventional balloon catheters such as disclosed in U.S. Pat. No. 4,323,071 have dilatation balloons with an axial length of between 1 and 2 cm. In treating long lesions, the conventional balloon is subject to multiple fragmented inflations where the balloon is inflated within the stenosis at one position and then deflated and moved axially within the stenosis to an adjoining position and reinflated to dilate the stenosis.

It has been suggested that the use of dilation catheters having a balloon with a length of 3.0 to 4.0 cm may improve the outcome of PTCA in lesions having a length greater than 2 cm. See Savas et al *Journal of American College of Cardiology*, 19 (3:34A) 1992. It is suggested that these so called "long balloons" will more evenly distribute pressure throughout the entire length of the diseased section. The long balloon also eliminates the need for repeated multiple fragmented inflations across the diseased segment, thereby reducing the risk of tissue injury.

Long balloons have recently been produced by Advanced Cardiovascular System (ACS) of Mountainview, Calif. ACS produces long balloons having a length of either 3.0 cm or 4.0 cm and the results from the use of long balloons appear to be superior to the results from using balloons of conventional lengths. However, risks remain of subsequent major cardiac events from PTCA in long lesions, particularly in vessels which are bent at an angle greater than about 45°.

SUMMARY OF THE INVENTION

The present invention is directed to reducing the risks of complications which can be associated with long lesions, and particularly with long lesions which occur on vessels having a large angle of bend. In accordance with the present invention, a dilation catheter is provided with a long balloon which when inflated has a working frusto-conical portion extending between a proximal end and a distal end of the balloon. The frusto-conical portion tapers inwardly from the proximal end to the distal end. The taper is preferably provided to conform to the anatomical shape of the vessel. It has been found that a suitable rate of taper for a balloon is about 0.1 to about 0.2 mm for each cm of length, preferably, about 0.125 mm to about 0.1825 mm for each cm of length.

DESCRIPTION OF THE DRAWINGS

The foregoing and other objects and advantages of the invention will be appreciated more fully from the following further description thereof, with reference to the accompanying drawings wherein:

FIG. 1 is a fragmented illustration of an over-the-wire balloon dilatation catheter having a tapered long balloon in accordance with the invention;

FIG. 2 is a cut away illustration of a vessel with a stenosis and the tapered long balloon in accordance with the invention;

FIG. 3 is a cross-sectional view of the tapered long balloon in accordance with the invention; and FIG. 4 is an illustration of a vessel with an acute bend and a tapered long balloon;

DESCRIPTION OF THE PREFERRED EMBODIMENT

A tapered long balloon 10 in accordance with the invention is shown in FIG. 1 in conjunction with a conventional over-the-wire catheter assembly 12. The tapered long balloon 10 is suited for use with all known types of catheters for percutaneous transluminal coronary angioplasty (PTCA). However, the tapered long balloon is disclosed herein with the over-the-wire catheter manufactured by Advanced Cardiovascular Systems, Inc. of Mountainview, Calif.

The catheter assembly 12 includes a guide wire 14, a dilatation catheter 16 and an inflation device 18. The guide wire 14 is formed of metal and is very small in diameter. The guide wire has a relatively stiff proximal portion 20 extending from a proximal end and a more flexible distal portion 24 which has a helical coil (not shown) at a distal end. Typical diameters of the guide wire 14 are in the range of about 0.01 to about 0.018 inches.

The dilatation catheter 16 has a relatively long catheter shaft 26 extending between a fitting 28 mounted on a proximal end and the tapered long balloon 10 adjacent a distal end portion 30 of the catheter shaft. The catheter shaft 26 is formed of relatively thin solid wall tubing. The catheter shaft 26 is quite long and may be in the order of 150 cm long and is axially flexible so that it will track over a guide wire as it is advanced through a patient's vasculature. The fitting 28 is in the form of a conventional threaded fitting and is adapted for connection to the inflation assembly 18.

The catheter shaft 26 has an axial lumen 32 dimensioned to freely accept the guide wire 14 as best shown in FIG. 3. The diameter of the lumen 32 at the distal end portion 30 of the catheter shaft is smaller than the diameter of the proximal end and the inner diameter of the lumen 32 is smaller so as to fit tightly about the guide wire 14 as best shown in FIG. 3. A plurality of perforations 34 are made in the catheter shaft in the portion which extends within the balloon. As will be discussed below, the perforations 34 permit pressurized fluid to be introduced from the inflation device 18 through the lumen of the catheter shaft into an inner chamber 36 of the balloon 10 to permit inflation of the balloon 10.

The catheter has a smooth coating 37 which extends over the catheter shaft to which the tapered long balloon 10 is secured. The balloon has a frusto-conical working section 38 extending between a proximal end 40 which is affixed to the coating of the catheter shaft 26 and a distal end 42 which is affixed to the distal end portion of the catheter assembly. The long balloon has a length L of at least 3 cm and may be greater up to 10 cm. The balloon has an outer diameter $D_1$ when dilated at its proximal end 40 which is greater than the diameter $D_2$ at its distal end 42. For many vessels it has been determined that the frusto-conical section of the balloon should be tapered at a rate of 0.125 mm per 1.0 cm, thus, for a balloon having a length of 4 cm and an outer diameter of 3.5 mm at the proximal end, the outer diameter of the distal end will be 3.0 cm.

It is important that the shape of the balloon be carefully controlled. Thus, the material of the balloon should be both expansible and sufficiently strong to maintain the predetermined tapered shape. It is believed that a suitable material for these purposes is polyethylene, polyethylene terephthalate or a polyolefinicionomer such as Surlyn ®, DuPont. It is believed that the shape may be maintained by varying the thickness of the wall so that it is not stretched out of shape. The balloon is affixed to the dilatation catheter by a suitable method such as gluing or heat welding.

Additionally, the balloon is provided with a marker 44 formed of a metal ribbon such as platinum which is helically wrapped onto the catheter shaft in the center of the balloon. The marker 44 permits the position of the balloon to be determined within the vascular structure by imaging by fluoroscopy.

It is believed that it may be necessary to have at least two different sized balloons. However, it is believed that the rate of taper for the different lengths and different outer diameters should be in a range of between 0.125 mm of diameter and 0.185 mm per 1 cm of length.

As shown in FIG. 1, the inflation device is connected to the lumen of the catheter shaft for the purpose of introducing fluid through the inflation device 18. The fluid, such as a radiographic contrast liquid, permits radiographic visualization of the balloon when inflated. The fluid is communicated through the lumen 32 around the guide wire 14 to perforations in the catheter shaft and into the balloon. In this manner, the balloon may be dilated as desired.

In operation, the catheter assembly is used by first inserting the guide wire 14 through a port 50 of the dilatation catheter. The dilatation catheter is then inserted through a guiding catheter (not shown) disposed within the brachial or femoral artery of the patient with the distal end seated within the ostium of the desired coronary artery. The guide wire is extended out the distal end of the guiding catheter into the patient's coronary artery to guide the catheter into the coronary artery. The balloon is positioned within a stenosis 52 to be dilated, as best shown in FIG. 2.

The balloon 10 is positioned by imaging the position of the marker within the stenosis 52. The balloon is then inflated by pumping the inflation device to direct pressurized fluid through the lumen 32 of the dilatation catheter into the balloon 10 to inflate the balloon, as best shown in FIGS. 2 or 4. The balloon may be inflated several times to effectively dilate the blood vessel. After sufficient inflations, the dilatation catheter and wire are removed from the artery.

Because coronary arteries typically taper and decrease in diameter as they extend away from the heart and because of the length of the balloon, it is believed to be particularly advantageous to taper the balloon to avoid dissection of the vessel and the possible abrupt closure thereof. Appropriate sizing of the balloon to the artery is critical if major cardiac complications (death, myocardial infarction, abrupt vessel closure or need for emergency bypass surgery) is to be avoided.

The widespread use of long ballons has previously been hampered because of a concern for occlusion of a side branch vessel 56 resulting from compression of plaque from the lesion into the lumen of the side branch 56.

However, it is believed that a tapered balloon will be particularly advantageous for use with stenoses over 2 cm long or in arteries which have a large angle of bend, such as shown in FIG. 4.

Regardless of lesion length, lesions located on bends are known to be associated with an increased risk when treated with balloon angioplasty. A conventional length balloon tends to straighten the natural artery bend leading to vessel trauma and injury. A long balloon conforms much better to the bend points of the vessel, thereby minimizing vessel trauma and injury. However, the vessel often tapers in size dramatically following the bend point. A long balloon, if sized correctly at its proximal portion, frequently is too large at its distal portion, leading to vessel tearing and injury. If the diameter of the balloon is narrowed in order to avoid dissection, there will be insufficient pressure at the proximal end of the stenosis to dilate the lesion and open the blood vessel. A tapered balloon leads to much improved results. Because the balloon conforms to the shape of the vessel, there should be less straightening of the bend in the vessel during inflation, thereby reducing iatrogenic trauma to the vessel.

While the invention has been described herein in terms of an over-the-wire balloon dilatation catheter, it will be clear to those skilled in the art that the invention is not limited by the description of the preferred embodiment and that the tapered long balloon of the invention is suitable for use with other dilatation catheter systems such as fixed wire catheters, perfusion type balloon catheters and rapid exchange type catheters.

Likewise, the tapered long balloon of the invention may be used advantageously to repair artery tears where balloons are used to "tack up" vessel dissection. A tapered balloon may be used to avoid increased dissection of the vessel at the narrower end of the vessel.

I claim:

1. A balloon dilatation catheter comprising:
   an elongated catheter shaft having an inflation lumen extending therethrough;
   a dilatation balloon on a distal section of said catheter shaft which has a working section with a first end and a second end spaced a predetermined distance apart, said predetermined distance being at least 30 mm, said first end having a first predetermined diameter when inflated and said second end having a second predetermined diameter when inflated which is smaller than said first diameter to provide a tapered working section said working section being tapered at a rate being generally within a range of about 0.125 mm/cm to about 0.185 mm/cm.

2. The balloon dilatation catheter of claim 1, wherein said first end of said balloon is a proximal end of said balloon and said second end is a distal end of said balloon.

3. A method of dilating a stenosis in a blood vessel comprising:
   forming an angioplasty balloon having a length of at least about 30 mm and a working section which when the balloon is inflated has a taper generally corresponding to the taper of said blood vessel; and
   advancing said balloon through a lumen in said stenosis such that said balloon extends outwardly from either end of said stenosis.

* * * * *

UNITED STATES PATENT AND TRADEMARK OFFICE
CERTIFICATE OF CORRECTION

PATENT NO. : 5,273,536
DATED : December 28, 1993
INVENTOR(S) : Vicky Savas

It is certified that error appears in the above-identified patent and that said Letters Patent is hereby corrected as shown below:

Column 2, line 23, delete "dilation" and insert

--dilatation--.

Signed and Sealed this

Twenty-first Day of June, 1994

Attest:

BRUCE LEHMAN

Attesting Officer     Commissioner of Patents and Trademarks